US00PP28029P3

(12) United States Plant Patent
van Kleinwee

(10) Patent No.: US PP28,029 P3
(45) Date of Patent: May 16, 2017

(54) *PETUNIA* PLANT NAMED 'PEHY0013'

(50) Latin Name: *Petunia hybrida*
Varietal Denomination: PEHY0013

(71) Applicant: SYNGENTA PARTICIPATIONS AG, Basel (CH)

(72) Inventor: Theodorus Cornelis van Kleinwee, Enkuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/757,333

(22) Filed: Dec. 17, 2015

(65) Prior Publication Data

US 2016/0198609 P1 Jul. 7, 2016

Related U.S. Application Data

(60) Provisional application No. 62/099,638, filed on Jan. 5, 2015.

(51) Int. Cl.
*A01H 5/02* (2006.01)

(52) U.S. Cl.
USPC ..... Plt./356.13

(58) Field of Classification Search
USPC ..... Plt./356.13
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0013' particularly distinguished by the large, violet flowers with a white center, deep green foliage, moderate branching, mounding to trailing plant habit, early flowering, vigorous and is floriferous throughout the season.

1 Drawing Sheet

Latin name of the genus and species of the plant claimed: *Petunia hybrida.*

Varietal denomination: 'PEHY0013'.

BACKGROUND OF THE NEW PLANT

The present invention comprises a new *Petunia*, botanically known as *Petunia hybrida*, and hereinafter referred to by the variety name 'PEHY0013'.

'PEHY0013' is a product of a planned breeding program. The new cultivar has large, violet flowers with a white center, deep green foliage, moderate branching, mounding to trailing plant habit, early flowering, vigorous and is floriferous throughout the season.

'PEHY0013' originated from a hybridization made in October 2010 in a controlled breeding environment in Enkhuizen, Netherlands.

The female parent was the commercial plant variety designated 'PEHY0003', U.S. Plant Pat. No. 23,644, with uniform purple flower color and more upright branching plant habit than 'PEHY0013'.

The male parent of 'PEHY0013' was a commercial plant variety named 'PEHY0008', U.S. Plant patent application Ser. No. 14/757,314, with purple colored flowers with a large white center, dark green foliage, and an improved branching habit than 'PEHY0013'.

The resulting seeds were sown in February 2011. 'PEHY0013' was selected as a single flowering plant within the progeny of the stated cross on May 25, 2011 in a controlled environment (greenhouse) in Enkhuizen, Netherlands.

The first act of asexual reproduction of 'PEHY0013' was accomplished when vegetative cuttings were propagated from the initial selection in June 2011 in a controlled environment in Enkhuizen, The Netherlands.

BRIEF SUMMARY OF INVENTION

Horticultural examination of plants grown from cuttings of the plant initiated in September 2011 in Angers, France, and continuing thereafter, has demonstrated that the combination of characteristics as herein disclosed for 'PEHY0013' are firmly fixed and are retained through successive generations of asexual reproduction.

'PEHY0013' has not been observed under all possible environmental conditions. The phenotype may vary significantly with variations in environment such as temperature, light intensity, and day length.

A Plant Breeder's Right for this cultivar was applied for in the European Community Plant Variety Office (CPVO) on Jun. 27, 2014, No. 2014/1721. 'PEHY0013' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0013' with colors being as true as possible with an illustration of this type.

Figure 1:
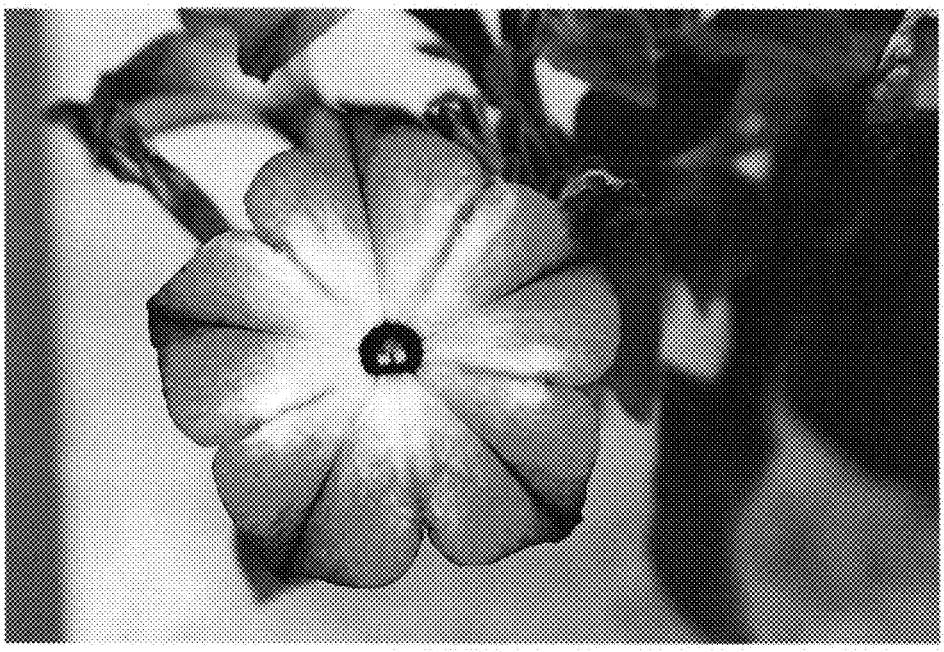
Figure 2:
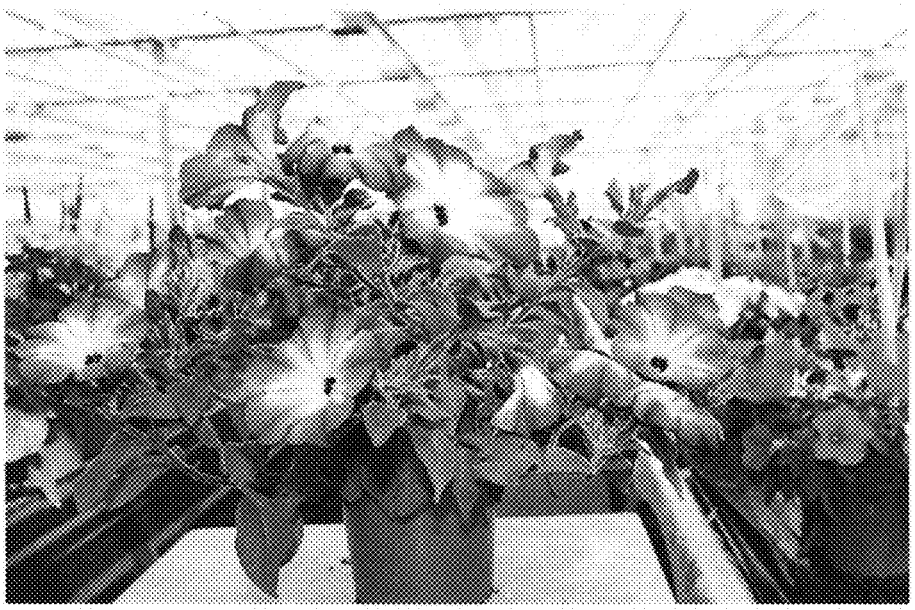

The photographic drawing shows in FIG. 2 a flowering plant of the new variety and in FIG. 1 a close-up of the flowers.

DETAILED BOTANICAL DESCRIPTION

The plant descriptions and measurements were taken around Oct. 1, 2014, from plants grown for breeding purposes in a greenhouse in Enkhuizen, Netherlands. The plants had been planted around Jul. 10, 2014. They were approximately 12 weeks of age and growing in 19 cm containers. They had been cut back a few weeks before the observations.

The aforementioned photographs were taken in April 2014 from plants growing in a greenhouse trial in Andijk, Netherlands. These plants were approximately 12-13 weeks of age.

Color references are made to The Royal Horticultural Society Colour Chart (R.H.S.) 2001.

TABLE 1

DIFFERENCES BETWEEN THE NEW VARIETY 'PEHY0013' AND A SIMILAR VARIETY

| | 'PEHY0013' | 'FORTUNIA PURPLE PICOTEE' |
|---|---|---|
| Flower color pattern: | Violet, RHS N87A near margin, and large, nearly white center | Deep violet, RHS 79B, with white margins |
| Flowering response: | Earlier | Later |
| Plant habit: | Taller, more vigorous | More compact |

Plant:

*Form, growth and habit.*—Mounding to trailing, vigorous.

*Plant height.*—10 cm.

*Plant height (inflorescence included).*—15 cm.

*Plant width.*—31 cm.

Roots:

*Number of days to initiate roots.*—About 12 days at about 22 degrees C.

*Number of days to produce a rooted cutting plant.*—18-24 days at about 22 degrees C.

*Type.*—Fine, fibrous, free branching.

*Color.*—RHS N155B.

Foliage:

*Arrangement of leaves.*—Simple leaf, opposite, sometimes decussate.

*Immature leaf, color upper surface.*—RHS 138A.

*Immature leaf, color lower surface.*—RHS 138B.

*Mature leaf, color upper surface.*—RHS 137A.

*Mature leaf, color lower surface.*—RHS 137C.

*Length.*—7 cm.

*Width.*—4 cm.

*Shape.*—Ovate.

*Base shape.*—Obtuse.

*Apex shape.*—Acute or obtuse.

*Margin.*—Entire.

*Texture, upper surface.*—Pubescent with hirsute and glandular hair.

*Texture, lower surface.*—Pubescent with hirsute and glandular hair.

*Color of veins, upper surface.*—RHS 138B.

*Color of veins, lower surface.*—RHS 143A.

*Petiole color.*—RHS 145A.

*Length.*—0.3 cm.

*Diameter.*—0.25 cm.

*Texture.*—Hirsute.

Stem:

*Quantity of main branches per plant.*—3-5.

*Color of stem.*—RHS 144A.

*Length of stem.*—10-14 cm.

*Diameter.*—0.4 cm.

*Length of internodes.*—0.3 cm.

*Texture.*—Much glandular hair.

*Color of pedicels.*—RHS 144A.

*Length.*—3-4 cm.

*Diameter.*—0.2-0.3 cm.

*Texture.*—Much glandular hair.

Inflorescence:

*Type of inflorescence.*—Single flowers, emerging from the upper nodes of the stem.

*Blooming habit.*—Continuously through the summer months.

*Quantity of flowers per plant.*—About 15-20.

*Lastingness of individual blooms on the plant.*—About 2 weeks, depending on temperature.

*Fragrance.*—Slight.

Bud (just when opening/showing color):

*Color.*—RHS 79B at the top, the tube is dull violet near RHS N79D mixed with pale green, RHS 145B; dark veins of RHS N92A.

*Length.*—5.0-5.5 cm.

*Width.*—0.8-2 cm at the top.

*Shape.*—Oblong.

Immature inflorescence:

*Diameter.*—5 cm.

*Vertical diamater.*—3.5 cm.

*Color upper surface.*—Between the tones of RHS N81A and RHS 83A, dark color at the margin, becoming lighter to towards the center.

*Color lower surface.*—RHS N81A with tones of RHS N81B to RHS N81C.

Mature inflorescence:

*Shape.*—Salver-shape, with funnel shape base, formed by 5 fused petals.

*Flower, horizontal diameter.*—7.5 cm.

*Flower, vertical diameter.*—About 6 cm.

*Flower color, upper surface.*—Violet with a large white, or nearly white center: RHS N87A to RHS N87B near the margin, and fading to tones of RHS 76A to RHS 76C, or even RHS N155A towards the center.

*Flower color, lower surface.*—A little more bluish and slightly duller than RHS 83D.

*Petal apex shape.*—Mucronulate.

*Petal base shape.*—Fused.

*Petal margin.*—Entire.

*Waviness of petals margin.*—Weak to medium.

*Petal lobation.*—Weak to medium.

*Texture, upper surface.*—Glabrous, papillose.

*Texture, lower surface.*—Papillose, mostly pubescent along veins and puberulous until one cm from the margin.

*Corolla tube, color inner side.*—RHS 83B with black veins.

*Corolla tube, color outer side.*—RHS 83C with many black veins.

*Corolla tube length.*—3.5 cm.

*Corolla tube, diameter.*—0.9 cm.

*Corolla tube, texture of outer surface.*—Pilose, glandular hair.

Calyx:

*Form.*—5 sepals in a whorl, fused at the base.

*Color, upper/outer surface.*—RHS 137A.

*Color, inner surface.*—RHS 137C.

*Length.*—2.4 cm.

*Width.*—0.6 cm.

*Shape*.—Ensiform, fused at the base.

*Apex shape*.—Acute.

*Based*.—Fused.

*Margins*.—Entire.

*Texture, upper surface*.—Hirsute.

*Texture, lower surface*.—Hirsute with shorter hair than upper surface.

Reproductive organs:

*Gynoecium*.—Pistil: 1. Length: 2.6 cm. Style color: RHS 143C, green at the base, to RHS 83A near the stigma. Style length: 2.4 cm. Stigma color: RHS 137B. Stigma shape: Flat rounded disc fixed on the style from under. Ovary color: RHS 143C.

*Androecium*.—Stamens: 5. Color of filaments: RHS N155A, white/grey, with purple shades near the anther RHS N82B. Length filaments: 2.4-2.8 cm. Anther color: RHS 199D with a blue grey strip in the middle. Anther length: 0.2 cm. Anther shape: Elliptical. Color of pollen: RHS 202B. Pollen amount: Plenty.

Fertility/seed set: Has not been observed on this hybrid.

Disease/pest resistance: Has not been observed on this hybrid.

What is claimed is:

1. A new and distinct variety of *Petunia* plant named 'PEHY0013' substantially as illustrated and described herein.

* * * * *